United States Patent
Wu et al.

(10) Patent No.: US 11,891,371 B2
(45) Date of Patent: Feb. 6, 2024

(54) PIPERONYLIC ACID DERIVATIVE AND PREPARATION AND APPLICATION THEREOF

(71) Applicants: SHENYANG SINOCHEM AGROCHEMICALS R&D CO., LTD., Liaoning (CN); JIANGSU YANGNONG CHEMICAL CO., LTD., Jiangsu (CN)

(72) Inventors: Hongfei Wu, Liaoning (CN); Jingbo Xu, Liaoning (CN); Shaowu Liu, Liaoning (CN); Haibo Yu, Liaoning (CN); Xiuhui Chang, Liaoning (CN); Qin Sun, Liaoning (CN); Libao Xu, Liaoning (CN); Xueming Cheng, Liaoning (CN); Hao Yang, Liaoning (CN); Ningning Sun, Liaoning (CN)

(73) Assignees: SHENYANG SINOCHEM AGROCHEMICALS R&D CO., LTD, Liaoning (CN); JIANGSU YANGNONG CHEMICAL CO., LTD., Jiangsu (CN)

( * ) Notice: Subject to any disclaimer, the term of this patent is extended or adjusted under 35 U.S.C. 154(b) by 0 days.

(21) Appl. No.: 16/625,296

(22) PCT Filed: Jun. 22, 2018

(86) PCT No.: PCT/CN2018/092393
§ 371 (c)(1),
(2) Date: Dec. 20, 2019

(87) PCT Pub. No.: WO2019/001361
PCT Pub. Date: Jan. 3, 2019

(65) Prior Publication Data
US 2020/0181107 A1 Jun. 11, 2020

(30) Foreign Application Priority Data

Jun. 29, 2017 (CN) .......................... 201710514218.2

(51) Int. Cl.
*C07D 317/68* (2006.01)
*A01N 43/30* (2006.01)
(52) U.S. Cl.
CPC ........... *C07D 317/68* (2013.01); *A01N 43/30* (2013.01)
(58) Field of Classification Search
CPC .............................. A01N 43/30; C07C 343/22
See application file for complete search history.

(56) References Cited

U.S. PATENT DOCUMENTS

| | | | |
|---|---|---|---|
| 8,563,736 B2 | 10/2013 | Yoshida et al. | |
| 8,853,440 B2 | 10/2014 | Aoki et al. | |
| 9,920,026 B2 | 3/2018 | Yoshida et al. | |
| 2007/0049635 A1 | 3/2007 | Ebihara et al. | |
| 2007/0275980 A1 | 11/2007 | Yoshida et al. | |
| 2009/0192167 A1 | 7/2009 | Nomura et al. | |
| 2014/0206727 A1 | 7/2014 | Yoshida et al. | |

FOREIGN PATENT DOCUMENTS

| | | | |
|---|---|---|---|
| AU | 2004315003 A1 | 12/2004 | |
| CN | 1628095 A | 6/2005 | |
| CN | 1863766 A | 11/2006 | |
| CN | 1926094 A | 3/2007 | |
| CN | 101203132 A | 6/2008 | |
| WO | 2005/073165 A1 | 8/2005 | |
| WO | WO-2019059412 A1 * | 3/2019 | ............. A01N 43/54 |

OTHER PUBLICATIONS

Cambridge medchem consulting (https://web.archive.org/web/20130113020012/https://www.cambridgemedchemconsulting.com/resources/bioisoteres/) no pagination. (Year: 2013).*
Patani, G. et al. "Bioisosterism: A Rational Approach in Drug Design" Chem. Rev., v. 96, 3147-3176. (Year: 1996).*
International Search Report for PCT/CN2018/092393, dated Sep. 3, 2018 (6pgs. with English translation).

* cited by examiner

*Primary Examiner* — Erin E Hirt
(74) *Attorney, Agent, or Firm* — Smith, Gambrell & Russell, LLP

(57) ABSTRACT

The present invention belongs to the fields of insecticides, acaricides and fungicides, and particularly relates to a piperonylic acid derivative, and preparation and application thereof. The structure is shown in a general formula I, and the definition of each substituent in the formula is described in the description. The compound of the general formula I exhibits excellent insecticidal, acaricidal and fungicidal activity and can be used for controlling various harmful insects, mites or fungus.

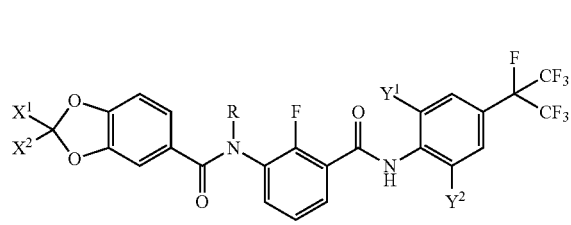

1 Claim, No Drawings

PIPERONYLIC ACID DERIVATIVE AND PREPARATION AND APPLICATION THEREOF

TECHNICAL FIELD

The present invention belongs to the fields of insecticides, acaricides and fungicides, and particularly relates to a piperonylic acid derivative, and preparation and application thereof.

BACKGROUND

Corresponding control objects will be resistant to the insecticides, acaricides or fungicides which are used for a period of time. Therefore, novel or improved insecticides, acaricides or fungicides and compositions thereof need to be continuously developed.

Structural modification with natural active molecules as leads is an important way to discover medicines and pesticides. There are few reports on the study of discovery of the pesticides by taking piperonylic acid of natural active component in pepper as a lead.

WO2005073165A1, US2007275980A1 and US20140206727A1 disclosed that the insecticidal compound $KC_1$ (compound number in the patent: compound 160) showed more than or equal to 70% mortality rates against *Spodoptera litura* and *Plutella xylostella* at 100 ppm.

[Structure of piperonylic acid]

[Structure of $KC_1$]

U.S. Pat. No. 8,853,440B2 disclosed that 4-heptafluoroisopropylaniline insecticidal compound $KC_2$ (Pesticide common name: Broflanilide, compound number in the patent: compound 3-1) and $KC_3$ (compound number in the patent: compound 3-14) exhibited more than or equal to 70% mortality rates against *Spodoptera litura* and *Plutella xylostella* at 1 ppm.

[Structure of $KC_2$]

[Structure of $KC_3$]

The present invention adopts a natural product, i.e., piperonylic acid, as a lead to obtain the compound of the general formula I by introducing an appropriate active substructure of 4-heptafluoroisopropylaniline, and obtains unexpectedly good biological activity results. The piperonylic acid derivative shown in the present invention and the insecticidal, acaricidal and fungicidal activities thereof have not been reported.

SUMMARY

The purpose of the present invention is to provide a piperonylic acid derivative, and preparation and application as an insecticide, an acaricide and a fungicide.

To achieve the above purpose, the present invention adopts the following technical solution:

A piperonylic acid derivative is shown in a general formula

[Structure of general formula I]

wherein:
$X_1$ is selected from halogens;
$X^2$ is selected from H or halogens;
R is selected from H, $C_1$-$C_3$ alkyl or $C_1$-$C_3$
$Y^1$ is selected from halogens or $C_1$-$C_3$ haloalkyl;
$Y^2$ is selected from halogens or $C_1$-$C_3$ haloalkyl.

A preferred compound in the present invention is: in the general formula I
$X^1$ is selected from F, Cl or Br;
$X^2$ is selected from H, F, Cl or Br;
R is selected from H, methyl or halomethyl;
$Y^1$ is selected from F, Cl, Br, I or halomethyl;
$Y^2$ is selected from F, Cl, Br, I or halomethyl.

A further preferred compound in the present invention is: in the general formula I
$X_1$ is selected from F;
$X^2$ is selected from H or F;
R is selected from H, methyl or halomethyl;
$Y^1$ is selected from F, Cl, Br, I or halomethyl;
$Y^2$ is selected from F, Cl, Br, I or halomethyl.

A more preferred compound in the present invention is: in the general formula I
$X^1$ is selected from F;
$X^2$ is selected from F;
R is selected from H or methyl;

$Y^1$ is selected from F, Cl, Br, I or halomethyl;
$Y^2$ is selected from F, Cl, Br, I or halomethyl.

A most preferred compound in the present invention is: in the general formula I
$X^1$ is selected from F;
$X^2$ is selected from F;
R is selected from H or methyl;
$Y^1$ is selected from F, Cl, Br or I;
$Y^2$ is selected from F, Cl, Br, I or halomethyl.

The present invention also comprises a compound shown in a general formula II,

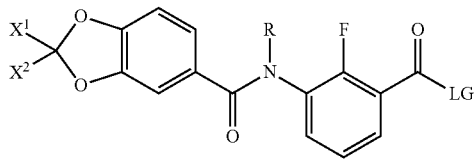

wherein:
$X_1$ is selected from halogens;
$X^2$ is selected from H or halogens;
R is selected from H, alkyl or $C_1$-$C_3$ haloalkyl;
LG is selected from $C_1$-$C_6$ alkoxyl, OH or halogens.

A preferred compound in the present invention is: in the general formula II
$X^1$ is selected from F, Cl or Br;
$X^2$ is selected from H, F, Cl or Br;
R is selected from H, methyl or halomethyl;
LG is selected from $C_1$-$C_6$ alkoxyl, OH or halogens.

A further preferred compound in the present invention is: in the general formula II
$X^1$ is selected from F;
$X^2$ is selected from H or F;
R is selected from H, methyl or halomethyl;
LG is selected from $C_1$-$C_6$ alkoxyl, OH or halogens.

A more preferred compound in the present invention is: in the general formula I
$X^1$ is selected from F;
$X^2$ is selected from F;
R is selected from H or methyl;
LG is selected from $C_1$-$C_3$ alkoxyl, OH, F, Cl, Br or The compound of the general formula I in the present invention can be prepared by the following method. Unless otherwise stated, the definitions of the groups in the formula are the same as above.

Method 1

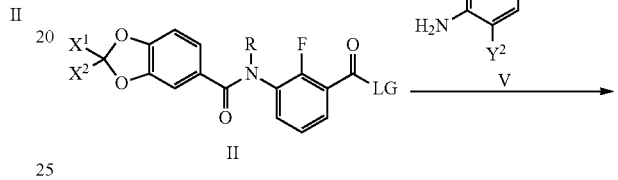

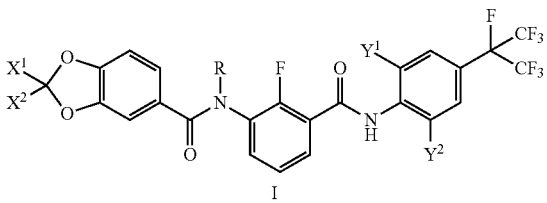

In the formula, LG in the compound of the general formula II is a leaving group such as E ($C_1$-$C_6$ alkoxyl) in the general formula II-a, OH in the general formula II-b or M (halogen) in the general formula II-c in the following formula. A specific synthesis method is as follows:

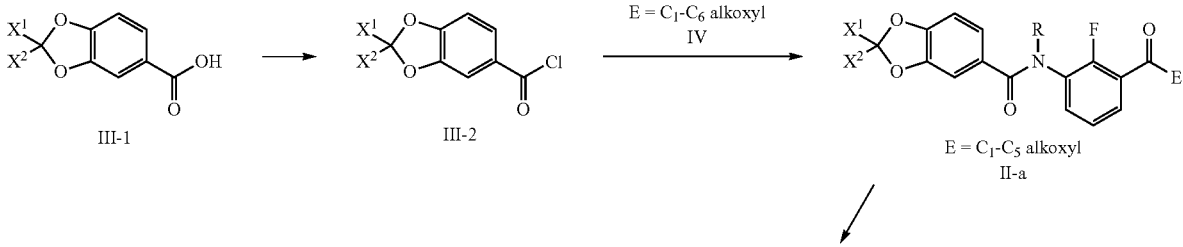

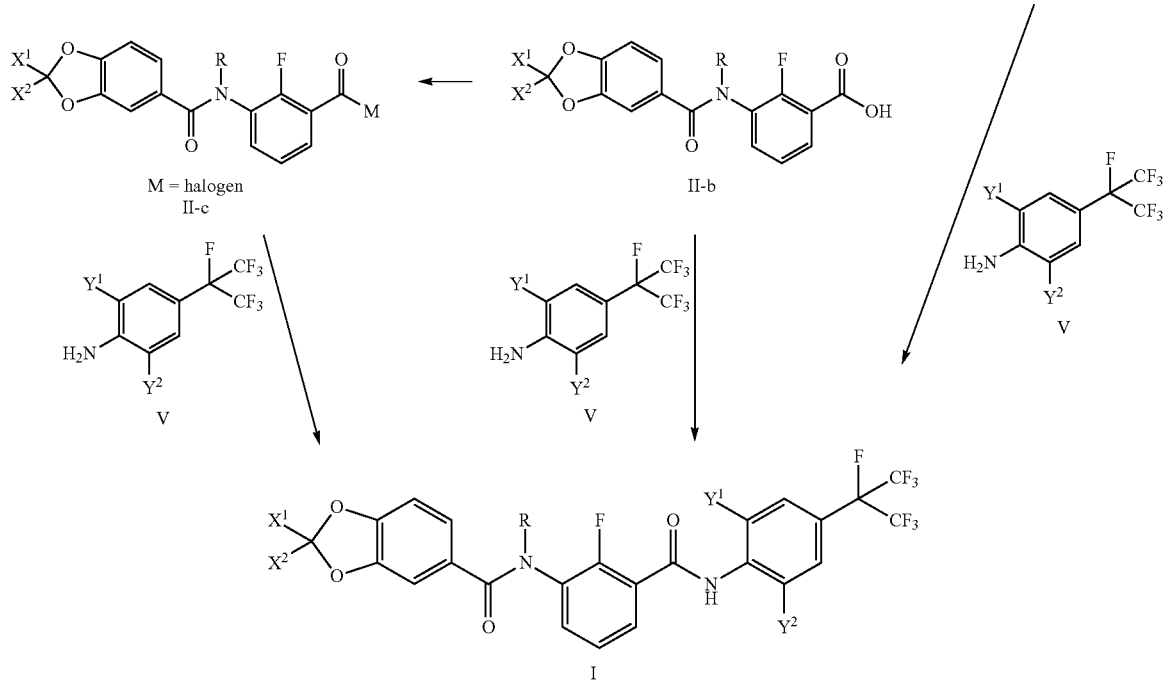

M = halogen
II-c

II-b

V

V

V

I

The compound of the general formula III-1 is acyl chlorinated with a proper acyl chloride reagent (such as oxalyl chloride and thionyl chloride) to obtain acyl chloride III-2, and the compound (substituted aniline) of the general formula IV is converted into the compound of the general formula II-a by acylation with acyl chloride III-2. The compound (substituted benzoate) of the general formula II-a is hydrolyzed to prepare the compound (substituted benzoic acid) of the general formula II-b. The compound (substituted benzoic acid) of the general formula II-b is acyl halogenated with a proper acyl halide reagent (such as oxalyl chloride, thionyl chloride, phosphorus in tribromide and phosphorus oxybromide) to obtain the compound (substituted benzoyl halide) of the general formula II-c, and the compound (substituted aniline) of the general formula V is converted into the compound of the general formula I by acylation with acyl halide the compound of the general formula II-c.

Or, the compound of the general formula II-a is converted into the compound of the general formula I by anlinolysis reaction with the compound of the general formula V.

Or, the compound of the general formula II-b is converted into the compound of the general formula I by condensation reaction with the compound of the general formula V.

Method 2

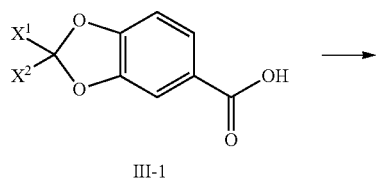

III-1

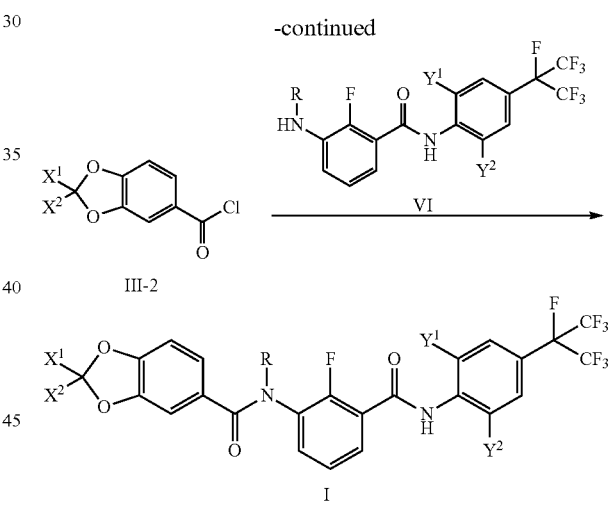

III-2

VI

I

The compound of the general formula III-1 is acyl chlorinated with a proper acyl chloride reagent (such as oxalyl chloride and thionyl chloride) to obtain acyl chloride III-2, and the compound (substituted aniline) of the general formula IV is converted into the compound of the general formula I by acylation with acyl chloride III-2.

In the definitions of the compounds of the general formulas provided above, the terms used in the collection generally represent the following substituents:

Halogen: F, Cl, Br or I.

Alkyl: linear, branched or cyclic alkyl, such as methyl, ethyl, n-propyl, isopropyl or cyclopropyl.

Haloalkyl: linear, branched or cyclic alkyl on which hydrogen atoms can be partially or fully replaced by the halogens, such as chloromethyl, dichloromethyl, trichloromethyl, fluoromethyl, difluoromethyl, trifluoromethyl, pentatluoroethyl or heptafluoroisopropyl.

Alkoxyl: linear, branched or cyclic alkoxyl, such as methoxyl, ethoxyl, n-propoxyl, isopropoxyl, cyclopropyloxyl or n-butoxyl.

The sources of raw materials and intermediates involved in the above preparation method are as follows:

Intermediate IV, intermediate V and intermediate VI can be prepared according to the method of U.S. Pat. No. 8,853,440B2.

Intermediate III-1, the acyl halide reagent, and other conventional raw materials and reagents are generally commercially available or can be prepared according to a conventional method.

In the compounds of the present invention, the compound of the general formula I is a chirality structural compound due to the difference between $X^1$ and $X^2$. In this case, the compounds may exist in a form of a single chirality isomer or a mixture of two chirality isomers. The compound shown in the general formula I as claimed by the present invention is not limited by the existence form of the above isomer structures.

The specific compounds listed in Table 1 can be used to illustrate the present invention, but not to limit the present invention.

TABLE 1

| No. | $X^1$ | $X^2$ | R | $Y^1$ | $Y^2$ |
|---|---|---|---|---|---|
| I-1 | F | F | H | I | I |
| I-2 | F | F | H | Br | $CF_3$ |
| I-3 | F | F | H | Cl | Cl |
| I-4 | F | F | H | F | F |
| I-5 | F | F | H | Br | I |
| I-6 | F | F | H | Br | Cl |
| I-7 | F | F | H | Br | F |
| I-8 | F | F | H | Br | Br |
| I-9 | F | F | H | I | Cl |
| I-10 | F | F | H | F | Cl |
| I-11 | F | F | H | F | I |
| I-12 | F | F | H | F | $CF_3$ |
| I-13 | F | F | H | Cl | $CF_3$ |
| I-14 | F | F | H | I | $CF_3$ |
| I-15 | F | F | H | $CF_3$ | $CF_3$ |
| I-16 | F | F | H | F | $CF_2CF_3$ |
| I-17 | F | F | H | F | $CF(CF_3)_2$ |
| I-18 | F | F | H | Br | $CF_2CF_3$ |
| I-19 | F | F | H | Br | $CF(CF_3)_2$ |
| I-20 | F | F | H | Cl | $CF_2CF_3$ |
| I-21 | F | F | H | Cl | $CF(CF_3)_2$ |
| I-22 | F | F | H | I | $CF_2CF_3$ |
| I-23 | F | F | H | I | $CF(CF_3)_2$ |
| I-24 | F | F | H | F | $CHF_2$ |
| I-25 | F | F | H | Cl | $CHF_2$ |
| I-26 | F | F | H | I | $CHF_2$ |
| I-27 | F | F | H | Br | $CHF_2$ |
| I-28 | F | F | H | F | $CH_2F$ |
| I-29 | F | F | H | Cl | $CH_2F$ |
| I-30 | F | F | H | I | $CH_2F$ |
| I-31 | F | F | H | Br | $CH_2F$ |
| I-32 | F | F | H | F | $CH_2Cl$ |
| I-33 | F | F | H | Cl | $CH_2Cl$ |
| I-34 | F | F | H | I | $CH_2Cl$ |
| I-35 | F | F | H | Br | $CH_2Cl$ |
| I-36 | F | F | H | F | $CH_2Br$ |
| I-37 | F | F | H | Cl | $CH_2Br$ |
| I-38 | F | F | H | I | $CH_2Br$ |
| I-39 | F | F | H | Br | $CH_2Br$ |
| I-40 | F | F | H | F | $CH_2I$ |
| I-41 | F | F | H | Cl | $CH_2I$ |
| I-42 | F | F | H | I | $CH_2I$ |
| I-43 | F | F | H | Br | $CH_2I$ |
| I-44 | F | F | $CH_3$ | I | I |
| I-45 | F | F | $CH_3$ | Br | $CF_3$ |
| I-46 | F | F | $CH_3$ | Cl | Cl |
| I-47 | F | F | $CH_3$ | F | F |
| I-48 | F | F | $CH_3$ | Br | I |
| I-49 | F | F | $CH_3$ | Br | Cl |
| I-50 | F | F | $CH_3$ | Br | F |
| I-51 | F | F | $CH_3$ | Br | Br |
| I-52 | F | F | $CH_3$ | I | Cl |
| I-53 | F | F | $CH_3$ | F | Cl |
| I-54 | F | F | $CH_3$ | F | I |
| I-55 | F | F | $CH_3$ | F | $CF_3$ |
| I-56 | F | F | $CH_3$ | Cl | $CF_3$ |
| I-57 | F | F | $CH_3$ | I | $CF_3$ |
| I-58 | F | F | $CH_3$ | $CF_3$ | $CF_3$ |
| I-59 | F | F | $CH_3$ | F | $CF_2CF_3$ |
| I-60 | F | F | $CH_3$ | F | $CF(CF_3)_2$ |
| I-61 | F | F | $CH_3$ | Br | $CF_2CF_3$ |
| I-62 | F | F | $CH_3$ | Br | $CF(CF_3)_2$ |
| I-63 | F | F | $CH_3$ | Cl | $CF_2CF_3$ |
| I-64 | F | F | $CH_3$ | Cl | $CF(CF_3)_2$ |
| I-65 | F | F | $CH_3$ | I | $CF_2CF_3$ |
| I-66 | F | F | $CH_3$ | I | $CF(CF_3)_2$ |
| I-67 | F | F | $CH_3$ | F | $CHF_2$ |
| I-68 | F | F | $CH_3$ | Cl | $CHF_2$ |
| I-69 | F | F | $CH_3$ | I | $CHF_2$ |
| I-70 | F | F | $CH_3$ | Br | $CHF_2$ |
| I-71 | F | F | $CH_3$ | F | $CH_2F$ |
| I-72 | F | F | $CH_3$ | Cl | $CH_2F$ |
| I-73 | F | F | $CH_3$ | I | $CH_2F$ |
| I-74 | F | F | $CH_3$ | Br | $CH_2F$ |
| I-75 | F | F | $CH_3$ | F | $CH_2Cl$ |
| I-76 | F | F | $CH_3$ | Cl | $CH_2Cl$ |
| I-77 | F | F | $CH_3$ | I | $CH_2Cl$ |
| I-78 | F | F | $CH_3$ | Br | $CH_2Cl$ |
| I-79 | F | F | $CH_3$ | F | $CH_2Br$ |
| I-80 | F | F | $CH_3$ | Cl | $CH_2Br$ |
| I-81 | F | F | $CH_3$ | I | $CH_2Br$ |
| I-82 | F | F | $CH_3$ | Br | $CH_2Br$ |
| I-83 | F | F | $CH_3$ | F | $CH_2I$ |
| I-84 | F | F | $CH_3$ | Cl | $CH_2I$ |
| I-85 | F | F | $CH_3$ | I | $CH_2I$ |
| I-86 | F | F | $CH_3$ | Br | $CH_2I$ |
| I-87 | Cl | Cl | H | I | I |
| I-88 | Cl | Cl | H | Br | $CF_3$ |
| I-89 | Cl | Cl | H | Cl | Cl |
| I-90 | Cl | Cl | H | F | F |
| I-91 | Cl | Cl | H | Br | I |
| I-92 | Cl | Cl | H | Br | Cl |
| I-93 | Cl | Cl | H | Br | F |
| I-94 | Cl | Cl | H | Br | Br |
| I-95 | Cl | Cl | H | I | Cl |
| I-96 | Cl | Cl | H | F | Cl |
| I-97 | Cl | Cl | H | F | I |
| I-98 | Cl | Cl | H | F | $CF_3$ |
| I-99 | Cl | Cl | H | Cl | $CF_3$ |
| I-100 | Cl | Cl | H | I | $CF_3$ |
| I-101 | Cl | Cl | H | $CF_3$ | $CF_3$ |
| I-102 | Cl | Cl | H | F | $CF_2CF_3$ |
| I-103 | Cl | Cl | H | F | $CF(CF_3)_2$ |
| I-104 | Cl | Cl | H | Br | $CF_2CF_3$ |
| I-105 | Cl | Cl | H | Br | $CF(CF_3)_2$ |
| I-106 | Cl | Cl | H | Cl | $CF_2CF_3$ |

TABLE 1-continued

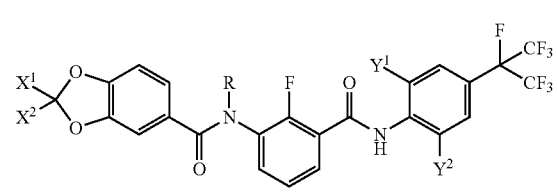

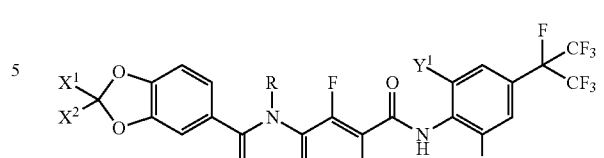

| No. | X¹ | X² | R | Y¹ | Y² |
|---|---|---|---|---|---|
| I-107 | Cl | Cl | H | Cl | CF(CF$_3$)$_2$ |
| I-108 | Cl | Cl | H | I | CF$_2$CF$_3$ |
| I-109 | Cl | Cl | H | I | CF(CF$_3$)$_2$ |
| I-110 | Cl | Cl | H | F | CHF$_2$ |
| I-111 | Cl | Cl | H | Cl | CHF$_2$ |
| I-112 | Cl | Cl | H | I | CHF$_2$ |
| I-113 | Cl | Cl | H | Br | CHF$_2$ |
| I-114 | Cl | Cl | H | F | CH$_2$F |
| I-115 | Cl | Cl | H | Cl | CH$_2$F |
| I-116 | Cl | Cl | H | I | CH$_2$F |
| I-117 | Cl | Cl | H | Br | CH$_2$F |
| I-118 | Cl | Cl | H | F | CH$_2$Cl |
| I-119 | Cl | Cl | H | Cl | CH$_2$Cl |
| I-120 | Cl | Cl | H | I | CH$_2$Cl |
| I-121 | Cl | Cl | H | Br | CH$_2$Cl |
| I-122 | Cl | Cl | H | F | CH$_2$Br |
| I-123 | Cl | Cl | H | Cl | CH$_2$Br |
| I-124 | Cl | Cl | H | I | CH$_2$Br |
| I-125 | Cl | Cl | H | Br | CH$_2$Br |
| I-126 | Cl | Cl | H | F | CH$_2$I |
| I-127 | Cl | Cl | H | Cl | CH$_2$I |
| I-128 | Cl | Cl | H | I | CH$_2$I |
| I-129 | Cl | Cl | H | Br | CH$_2$I |
| I-130 | Cl | Cl | CH$_3$ | I | I |
| I-131 | Cl | Cl | CH$_3$ | Br | CF$_3$ |
| I-132 | Cl | Cl | CH$_3$ | Cl | Cl |
| I-133 | Cl | Cl | CH$_3$ | F | F |
| I-134 | Cl | Cl | CH$_3$ | Br | I |
| I-135 | Cl | Cl | CH$_3$ | Br | Cl |
| I-136 | Cl | Cl | CH$_3$ | Br | F |
| I-137 | Cl | Cl | CH$_3$ | Br | Br |
| I-138 | Cl | Cl | CH$_3$ | I | Cl |
| I-139 | Cl | Cl | CH$_3$ | F | Cl |
| I-140 | Cl | Cl | CH$_3$ | F | I |
| I-141 | Cl | Cl | CH$_3$ | F | CF$_3$ |
| I-142 | Cl | Cl | CH$_3$ | Cl | CF$_3$ |
| I-143 | Cl | Cl | CH$_3$ | I | CF$_3$ |
| I-144 | Cl | Cl | CH$_3$ | CF$_3$ | CF$_3$ |
| I-145 | Cl | Cl | CH$_3$ | F | CF$_2$CF$_3$ |
| I-146 | Cl | Cl | CH$_3$ | F | CF(CF$_3$)$_2$ |
| I-147 | Cl | Cl | CH$_3$ | Br | CF$_2$CF$_3$ |
| I-148 | Cl | Cl | CH$_3$ | Br | CF(CF$_3$)$_2$ |
| I-149 | Cl | Cl | CH$_3$ | Cl | CF$_2$CF$_3$ |
| I-150 | Cl | Cl | CH$_3$ | Cl | CF(CF$_3$)$_2$ |
| I-151 | Cl | Cl | CH$_3$ | I | CF$_2$CF$_3$ |
| I-152 | Cl | Cl | CH$_3$ | I | CF(CF$_3$)$_2$ |
| I-153 | Cl | Cl | CH$_3$ | F | CHF$_2$ |
| I-154 | Cl | Cl | CH$_3$ | Cl | CHF$_2$ |
| I-155 | Cl | Cl | CH$_3$ | I | CHF$_2$ |
| I-156 | Cl | Cl | CH$_3$ | Br | CHF$_2$ |
| I-157 | Cl | Cl | CH$_3$ | F | CH$_2$F |
| I-158 | Cl | Cl | CH$_3$ | Cl | CH$_2$F |
| I-159 | Cl | Cl | CH$_3$ | I | CH$_2$F |
| I-160 | Cl | Cl | CH$_3$ | Br | CH$_2$F |
| I-161 | Cl | Cl | CH$_3$ | F | CH$_2$Cl |
| I-162 | Cl | Cl | CH$_3$ | Cl | CH$_2$Cl |
| I-163 | Cl | Cl | CH$_3$ | I | CH$_2$Cl |
| I-164 | Cl | Cl | CH$_3$ | Br | CH$_2$Cl |
| I-165 | Cl | Cl | CH$_3$ | F | CH$_2$Br |
| I-166 | Cl | Cl | CH$_3$ | Cl | CH$_2$Br |
| I-167 | Cl | Cl | CH$_3$ | I | CH$_2$Br |
| I-168 | Cl | Cl | CH$_3$ | Br | CH$_2$Br |
| I-169 | Cl | Cl | CH$_3$ | F | CH$_2$I |
| I-170 | Cl | Cl | CH$_3$ | Cl | CH$_2$I |
| I-171 | Cl | Cl | CH$_3$ | I | CH$_2$I |
| I-172 | Cl | Cl | CH$_3$ | Br | CH$_2$I |
| I-173 | F | H | H | Br | CF$_3$ |
| I-174 | F | H | H | Br | I |
| I-175 | F | H | H | Br | Br |
| I-176 | F | H | H | Br | Cl |
| I-177 | F | H | CH$_3$ | Br | CF$_3$ |
| I-178 | F | H | CH$_3$ | Br | I |
| I-179 | F | H | CH$_3$ | Br | Br |
| I-180 | F | H | CH$_3$ | Br | Cl |
| I-181 | F | H | H | Cl | Cl |
| I-182 | F | H | CH$_3$ | F | F |
| I-183 | F | H | CH$_3$ | I | I |
| I-184 | F | H | H | Cl | CF$_3$ |
| I-185 | Br | Br | H | Br | CF$_3$ |
| I-186 | Br | Br | H | Br | I |
| I-187 | Br | Br | H | Br | Br |
| I-188 | Br | Br | H | Br | Cl |
| I-189 | Br | Br | CH$_3$ | Br | CF$_3$ |
| I-190 | Br | Br | CH$_3$ | Br | I |
| I-191 | Br | Br | CH$_3$ | Br | Br |
| I-192 | Br | Br | CH$_3$ | Br | Cl |
| I-193 | Br | Br | H | Cl | Cl |
| I-194 | Br | Br | CH$_3$ | F | F |
| I-195 | Br | Br | CH$_3$ | I | I |
| I-196 | Br | Br | H | Cl | CF$_3$ |
| I-197 | I | I | H | Cl | CF$_3$ |
| I-198 | I | I | H | CF$_3$ | CF$_3$ |
| I-199 | I | I | H | Br | CF$_3$ |
| I-200 | I | I | H | Br | Br |
| I-201 | I | I | H | Br | I |
| I-202 | I | I | H | F | Br |
| I-203 | I | I | H | F | CF$_3$ |
| I-204 | I | I | H | Cl | Br |

$^1$H NMR (300 MHz, CDCl$_3$, ppm) and physicochemical properties of some compounds are as follows:

| Compound | $^1$H NMR Data | Physical Property |
|---|---|---|
| I-2 | 8.20 (s, 1H), 7.99 (s, 1H), 7.47 (d, 1H), 7.38(s, 1H), 6.96-6.80 (m, 4H), 6.71-6.65(m, 1H). | White Solid |
| I-5 | 8.62-8.57 (m, 1H), 8.12-8.05 (m, 3H), 7.96-7.91 (m, 2H), 7.70-7.68 (m, 2H), 7.42-7.36 (m, 1H), 7.21 (d, 1H). | White Solid |
| I-8 | 8.57-8.52 (m,1H), 8.17-8.12 (m, 2H), 7.90-7.86 (m, 3H), 7.70-7.68 (m, 2H), 7.39-7.34 (m 1H), 7.20 (d, 1H). | White Solid |
| I-44 | 8.08-8.03 (m, 2H), 7.86 (fs, 2H), 7.45-7.41 (m, 1H), 7.33-7.28 (m, 1H), 7.20 (s, 1H), 7.05 (d, 1H). 6.90 (d, 1H), 3.50 (s, 3H). | White Solid |
| I-45 | 8.13-8.04 (m, 3H), 7.91(s, 1H), 7.52-7.47 (m, 1H), 7.37-7.31 (m, 1H), 7.20 (s, 1H), 7.02 (d, 1H), 6.87 (d, 1H), 3.51 (s, 3H). | White Solid |

-continued

| Compound | $^1$H NMR Data | Physical Property |
|---|---|---|
| I-48 | 8.10-8.03 (m, 3H), 7.89 (s, 1H), 7.49-7.44 (m, 1H), 7.35-7.30 (m, 1H), 7.20 (s, 1H), 7.05 (d, 1H), 6.88 (d, 1H), 3.50 (s, 3H). | White Solid |
| I-51 | 8.09-8.04 (m, 2H), 7.87 (s, 2H), 7.47-7.43 (m, 1H), 7.34-7.29 (m, 1H), 7.20 (s, 1H), 7.05 (d, 1H), 6.89 (d, 1H), 3.50 (s, 3H). | White Solid |

At the same time, the specific compounds listed in Table 2 are the compounds of the general formula II in the reaction formula of the above preparation method 1, and can be used to illustrate the present invention, but not to limit the present invention.

TABLE 2

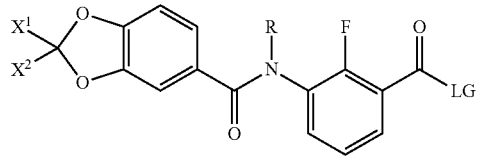

II

| No. | $X^1$ | $X^2$ | R | LG |
|---|---|---|---|---|
| II-1 | F | F | H | $OCH_3$ |
| II-2 | F | F | H | $OCH_2CH_3$ |
| II-3 | F | F | H | $OCH_2CH_2CH_3$ |
| II-4 | F | F | H | $OCH(CH_3)_2$ |
| II-5 | F | F | H | $OCH_2CH_2CH_2CH_3$ |
| II-6 | F | F | H | $OC(CH_3)_3$ |
| II-7 | F | F | H | OH |
| II-8 | F | F | H | F |
| II-9 | F | F | H | Cl |
| II-10 | F | F | H | Br |
| II-11 | F | F | H | I |
| II-12 | F | F | $CH_3$ | $OCH_3$ |
| II-13 | F | F | $CH_3$ | $OCH_2CH_3$ |
| II-14 | F | F | $CH_3$ | $OCH_2CH_2CH_3$ |
| II-15 | F | F | $CH_3$ | $OCH(CH_3)_2$ |
| II-16 | F | F | $CH_3$ | $OCH_2CH_2CH_2CH_3$ |
| II-17 | F | F | $CH_3$ | $OC(CH_3)_3$ |
| II-18 | F | F | $CH_3$ | OH |
| II-19 | F | F | $CH_3$ | F |
| II-20 | F | F | $CH_3$ | Cl |
| II-21 | F | F | $CH_3$ | Br |
| II-22 | F | F | $CH_3$ | I |
| II-23 | F | H | H | $OCH_3$ |
| II-24 | F | H | H | $OCH_2CH_3$ |
| II-25 | F | H | H | $OCH_2CH_2CH_3$ |
| II-26 | F | H | H | $OCH(CH_3)_2$ |
| II-27 | F | H | H | $OCH_2CH_2CH_2CH_3$ |
| II-28 | F | H | H | $OC(CH_3)_3$ |
| II-29 | F | H | H | OH |
| II-30 | F | H | H | F |
| II-31 | F | H | H | Cl |
| II-32 | F | H | H | Br |
| II-33 | F | H | H | I |
| II-34 | F | H | $CH_3$ | $OCH_3$ |
| II-35 | F | H | $CH_3$ | $OCH_2CH_3$ |
| II-36 | F | H | $CH_3$ | $OCH_2CH_2CH_3$ |
| II-37 | F | H | $CH_3$ | $OCH(CH_3)_2$ |
| II-38 | F | H | $CH_3$ | $OCH_2CH_2CH_2CH_3$ |
| II-39 | F | H | $CH_3$ | $OC(CH_3)_3$ |
| II-40 | F | H | $CH_3$ | OH |
| II-41 | F | H | $CH_3$ | F |
| II-42 | F | H | $CH_3$ | Cl |
| II-43 | F | H | $CH_3$ | Br |
| II-44 | F | H | $CH_3$ | I |
| II-45 | Cl | Cl | H | $OCH_3$ |
| II-46 | Cl | Cl | H | $OCH_2CH_3$ |
| II-47 | Cl | Cl | H | $OCH_2CH_2CH_3$ |
| II-48 | Cl | Cl | H | $OCH(CH_3)_2$ |
| II-49 | Cl | Cl | H | $OCH_2CH_2CH_2CH_3$ |
| II-50 | Cl | Cl | H | $OC(CH_3)_3$ |
| II-51 | Cl | Cl | H | OH |
| II-52 | Cl | Cl | H | F |
| II-53 | Cl | Cl | H | Cl |
| II-54 | Cl | Cl | H | Br |
| II-55 | Cl | Cl | H | I |
| II-56 | Cl | Cl | $CH_3$ | $OCH_3$ |
| II-57 | Cl | Cl | $CH_3$ | $OCH_2CH_3$ |
| II-58 | Cl | Cl | $CH_3$ | $OCH_2CH_2CH_3$ |
| II-59 | Cl | Cl | $CH_3$ | $OCH(CH_3)_2$ |
| II-60 | Cl | Cl | $CH_3$ | $OCH_2CH_2CH_2CH_3$ |
| II-61 | Cl | Cl | $CH_3$ | $OC(CH_3)_3$ |
| II-62 | Cl | Cl | $CH_3$ | OH |
| II-63 | Cl | Cl | $CH_3$ | F |
| II-64 | Cl | Cl | $CH_3$ | Cl |
| II-65 | Cl | Cl | $CH_3$ | Br |
| II-66 | Cl | Cl | $CH_3$ | I |
| II-67 | Br | Br | H | $OCH_3$ |
| II-68 | Br | Br | H | $OCH_2CH_3$ |
| II-69 | Br | Br | H | $OCH_2CH_2CH_3$ |
| II-70 | Br | Br | H | $OCH(CH_3)_2$ |
| II-71 | Br | Br | H | $OCH_2CH_2CH_2CH_3$ |
| II-72 | Br | Br | H | $OC(CH_3)_3$ |
| II-73 | Br | Br | H | OH |
| II-74 | Br | Br | H | F |
| II-75 | Br | Br | H | Cl |
| II-76 | Br | Br | H | Br |
| II-77 | Br | Br | H | I |
| II-78 | Br | Br | $CH_3$ | $OCH_3$ |
| II-79 | Br | Br | $CH_3$ | $OCH_2CH_3$ |
| II-80 | Br | Br | $CH_3$ | $OCH_2CH_2CH_3$ |
| II-81 | Br | Br | $CH_3$ | $OCH(CH_3)_2$ |
| II-82 | Br | Br | $CH_3$ | $OCH_2CH_2CH_2CH_3$ |
| II-83 | Br | Br | $CH_3$ | $OC(CH_3)_3$ |
| II-84 | Br | Br | $CH_3$ | OH |
| II-85 | Br | Br | $CH_3$ | F |
| II-86 | Br | Br | $CH_3$ | Cl |
| II-87 | Br | Br | $CH_3$ | Br |
| II-88 | Br | Br | $CH_3$ | I |
| II-89 | I | I | H | $OCH_3$ |
| II-90 | I | I | H | $OCH_2CH_3$ |
| II-91 | I | I | H | $OCH_2CH_2CH_3$ |
| II-92 | I | I | H | $OCH(CH_3)_2$ |
| II-93 | I | I | H | $OCH_2CH_2CH_2CH_3$ |
| II-94 | I | I | H | $OC(CH_3)_3$ |
| II-95 | I | I | H | OH |
| II-96 | I | I | H | F |
| II-97 | I | I | H | Cl |
| II-98 | I | I | H | Br |
| II-99 | I | I | H | I |
| II-100 | I | I | $CH_3$ | $OCH_3$ |
| II-101 | I | I | $CH_3$ | $OCH_2CH_3$ |
| II-102 | I | I | $CH_3$ | $OCH_2CH_2CH_3$ |
| II-103 | I | I | $CH_3$ | $OCH(CH_3)_2$ |
| II-104 | I | I | $CH_3$ | $OCH_2CH_2CH_2CH_3$ |
| II-105 | I | I | $CH_3$ | $OC(CH_3)_3$ |

TABLE 2-continued

[Structure II: benzodioxole with X¹, X² substituents connected to a carboxamide with R group on N, linked to a fluorobenzene with C(=O)LG group]

| No. | X¹ | X² | R | LG |
|---|---|---|---|---|
| II-106 | I | I | CH₃ | OH |
| II-107 | I | I | CH₃ | F |
| II-108 | I | I | CH₃ | Cl |
| II-109 | I | I | CH₃ | Br |

$^1$H NMR (300 MHz, CDCl$_3$, ppm) and physicochemical properties of some compounds are as follows:

| Compound | $^1$H NMR Data | Physical Property |
|---|---|---|
| II-1 | 10.15 (s, 1H), 7.93-7.87 (m, 3H), 7.74-7.69 (m, 1H) 7.41 (d, 1H), 7.34-7.28 (m, 1H), 3.89 (s, 3H). | White Solid |
| II-7 | 13.18 (br. s, 1H), 10.21 (s, 1H), 7.95-7.90 (m, 2H), 7.84-7.80 (m, 1H), 7.74-7.69 (m, 1H), 7.51 (d, 1H), 7.31-7.26 (m, 1H). | White Solid |
| II-9 | 8.80-8.75 (m, 1H), 8.05 (br. s, 1H), 7.90-7.85 (m, 1H), 7.66-7.64 (m, 2H), 7.39-7.33 (m 1H), 7.20 (d, 1H). | White Solid |
| II-12 | 7.86-7.80 (m, 1H), 7.26-7.22 (m, 1H), 7.14-7.09 (m, 2H), 7.03 (d, 1H), 6.85 (d, 1H), 3.94 (s, 3H), 3.42 (s, 3H). | White Solid |
| II-18 | 13.09 (br. s, 1H), 7.86-7.83 (m, 1H), 7.76-7.71 (m, 2H), 7.59-7.55 (m, 1H), 7.39 (d, 1H), 7.21-7.16 (m, 114), 3.32 (s, 3H). | White Solid |

In organic molecules, due to the difference in electronegativity, volume or spatial configuration of the substituents, the entire molecule may have a great difference in the transport properties or binding to the receptors in organisms such as insects and plants, and may also show a great difference in biological activity. The transport properties and suitability for binding to the receptors in the molecule are unpredictable and can be known by a lot of creative labor.

Compared with the known compounds KC$_1$, KC$_2$ or KC$_3$, the piperonylic acid derivative (the compound of the general formula I) of the present invention has unexpected high insecticidal activity and high acaricidal activity, and can control the following pests: lepidopteran pests such as armyworm, beet armyworm and diamondback moth; homopteran pests such as green peach aphid, leafhopper and plant hopper; hemipteran pests such as corn chinch bug, tomato fleahopper and rice skunk; thysanoptera pests such as Thrips tabaci lindemen, alfalfa thrips and soybean thrips; coleoptera pests such as potato beetles and elateridae; diptera pests such as flies and mosquitoes; hymenoptera pests such as bees and ants. The piperonylic acid derivative can control the following mites: tetranychidae (*Tetranychus urticae koch, tetranychus cinnabarinus, Panonychus uhni* and *Panonychus citri*), eriophyidae and tarsonemidae. Therefore, the present invention also comprises a purpose of the compound of the general formula I for controlling pests and mites in the fields of agriculture, forestry and sanitation.

The piperonylic acid derivative of the present invention shows high fungicidal activity, and can control the following diseases: rice blast, late blight, gray mold, powdery mildew, anthracnose and downy mildew. Therefore, the present invention also comprises a purpose of the compound of the general formula I for controlling diseases in the fields of agriculture, forestry and sanitation.

The present invention also comprises an insecticidal, acaricidal and fungicidal composition which comprises the compound shown in the above general formula I and an acceptable carrier in the field of agriculture, forestry or sanitation. The compound shown in the general formula I is taken as an active component, and the weight percentage content of the active component in the composition is 0.1-99%, The composition may include the compound shown in the above general formula I in the existence form of the isomer structures.

The composition may be used in the form of dry powder, wettable powder, an emulsifiable concentrate, a microemulsion, a paste, a granule, a solution, a suspending agent, etc., and the selection of the type of the composition depends on the specific application.

The composition is prepared in a known manner, for example by diluting or dissolving the active substance with a solvent medium and/or a solid diluent, optionally in the presence of a surfactant.

An available solid diluent or carrier can be silica, kaolin, bentonite, talc, diatomite, dolomite, calcium carbonate, magnesia, chalk, clay, synthetic silicate, attapulgite, sepiolite, etc.

In addition to water, available liquid diluents are aromatic organic solvents (a mixture of xylene or aikylbenzene, chlorobenzene, etc.), paraffins (petroleum fractions), alcohols (methanol, propanol, butanol, octanol and glycerol), esters (ethyl acetate and isobutyl acetate), ketones (cyclohexanorie, acetone, acetophenone, isophorone and ethyl amyl ketone) and amides (N, N-dimethylformamide and N-methylpyrrolidone).

Available surfactants are alkyl sulfonate, alkylaryl sulfonate, alkylphenol ethoxylate, polyoxyethylene sorbitan fatty acid ester and lignosulfonate.

The composition can also comprise special additives for specific purposes such as binders, e.g. gum arabic, polyvinyl alcohol and polyvinylpyrrolidone.

The concentration of the active component in the above composition may vary within a wide range according to the active component, the use objective, environmental conditions and the type of the adopted formulation. Generally, the concentration range of the active component is 1-90%, preferably 5-50%.

The technical solution of the present invention also comprises a method for controlling pests: applying the insecticidal composition of the present invention to a pest or a growth medium of the pest. The more appropriate effective dose which is often selected is 10 to 1000 grams per hectare, and preferably, the effective dose is 20 to 500 grams per hectare.

The technical solution of the present invention also comprises a method for controlling mites: applying the insecticidal composition of the present invention to a mite or a growth medium of the mite. The more appropriate effective dose which is often selected is 10 to 1000 grams per hectare, and preferably, the effective dose is 20 to 500 grams per hectare.

The technical solution of the present invention also comprises a method for controlling diseases: applying the insecticidal composition of the present invention to a disease or a growth medium of the disease. The more appropriate effective dose which is often selected is 10 to 1000 grams per hectare, and preferably, the effective dose is 20 to 500 grains per hectare.

For some applications, for example in agriculture, the addition of one or more other fungicides, insecticides, acaricides, herbicides, plant growth regulators or fertilizers to the insecticidal, acaricidal and fungicidal composition of the present invention can produce additional advantages and effects.

It should be understood that various modifications and changes can be made within the scope limited by claims of the present invention.

The present invention has the following advantages:

The present invention adopts a natural product, i.e., piperonylic acid, as a lead to obtain the compound of the general formula I by introducing an appropriate active substructure of 4-heptafluoroisopropylaniline. Because new structures are introduced, the opportunity for interaction and binding of molecules and receptors is enhanced, and unexpectedly good biological activity results in insecticidal, acaricidal and fungicidal activities are obtained, so that the piperonylic acid derivative obtained by the present invention has more comprehensive biological characteristics.

DETAILED DESCRIPTION

The following specific embodiments are used to further illustrate the present invention, but the present invention is not limited to these examples.

Synthesis Embodiments

Embodiment 1: Preparation of Compound 1-45

1) Preparation of N-(2-bromo-4-heptafluoroisopropyl-6-trifluoromethylphenyl)-2-fluoro-3-nitrobenzamide

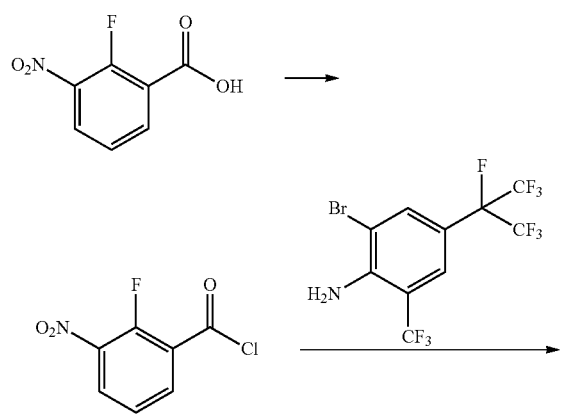

-continued

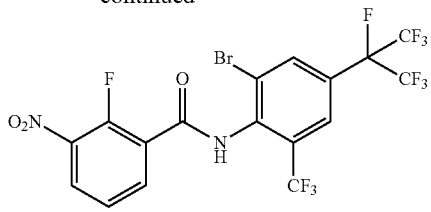

2-fluoro-3-nitrobenzoic acid (9.72 g, 52.4 mmol), thionyl chloride (40.05 g) and DMF (0.40 g) were added to a reaction flask. The reaction mixture was heated to 80° C. to react for 8 hours, and decompressed to distill off thionyl chloride to obtain acid chloride. 1,3-dimethyl-2-imidazolidinone (160 mL), 2-promo-4-heptafluoroisopropyl-6-trifluoromethylaniline (16.40 g, 40.0 mmol) and potassium iodide (1.68 g) were added, and the resulting mixture was heated to 100° C. to react for 48 hours. The reaction solution was cooled to room temperature, and filtered to remove insolubles. Ethyl acetate (100 mL) was added to dissolve. The resulting solution was washed successively with a saturated aqueous sodium bicarbonate solution and saturated salt solution to separate an organic phase. The organic phase was dried over anhydrous magnesium sulfate, filtered and decompressed to distill off organic solvents. The residue was purified by column chromatography on silica gel to obtain 2.10 g of the target compound as a white solid, with 9% yield (calculated based on the 2-bromo-4-heptafluoroisopropyl-6-trifitioromethylaniline).

$^1$H NMR (300 MHz, CDCl$_3$, ppm): 8.47-8.42 (m, 1H), 8.32-8.26 (m, 1H), 8.21 (d, 1H), 8.17 (s, 1H), 7.94 (s, 1H), 7.55-7.49 (m, 1H).

2) Preparation of N-(2-bromo-4-heptafluoroisopropyl-6-trifluoromethylphenyl)-3-amino-2-fluorobenzamide

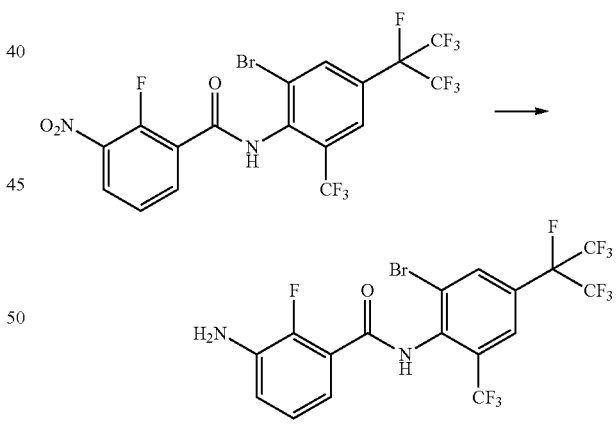

To the reaction flask, N-(2-bromo-4-heptafluoroisopropyl-6-trifluoromethylphenyl)-2-fluoro-3-nitrobenzamide (1.44 g, 2.5 mmol), dioxane (10 mL) and stannous chloride (2.28 g, 10.0 mmol) were added, and then concentrated hydrochloric acid (2 mL) was slowly added dropwise. The reaction mixture WM heated to 60-65° C. to react. After the reaction was complete by Thin-Layer Chromatography monitoring, the mixture was cooled to room temperature, and poured into ice water (15 mL). Ethyl acetate (30 mL) was added. Sodium hydroxide was slowly added to neutralize to pH=8-9. After the resulting mixture with precipitate was filtered through diatomite, the filter cake was washed with ethyl acetate and the filtrate was layered. The organic phase was dried over anhydrous magnesium sulfate and decompressed to distill off organic solvents. The residue was purified by column chromatography on silica gel to obtain 1.26 g of the target compound as a yellow solid, with 91% yield.

$^1$H NMR (300 MHz, CDCl$_3$, ppm): 8.29 (d, 1H), 8.13 (s, 1H), 7.91 (s, 1H), 7.50-7.44 (m, 1H), 7.12-7.07 (m, 1H), 7.04-6.94 (m, 1H), 3.93 (br. s, 2H).

3) Preparation of N-(2-bromo-4-heptafluoroisopropyl-6-trifluoromethyl phenyl)-2-fluoro-3-methylaminobenzamide

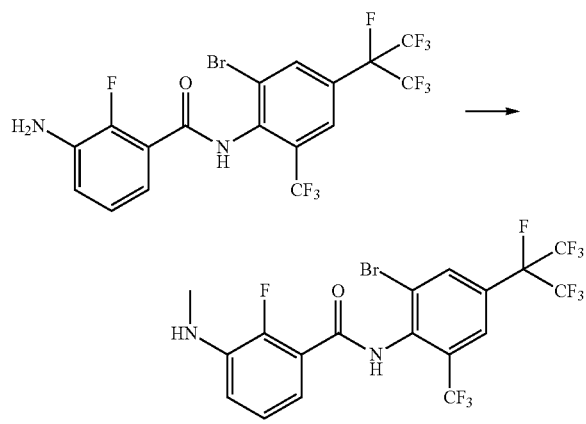

Concentrated sulfuric acid (3 mL) and N-(2-bromo-4-heptafluoroisopropyl-6-trifluoromethyl phenyl)-3-amino-2-fluorobenzamide (0.55 g, 1.0 mmol) were added to the reaction flask, and fully stirred for dissolving. Aqueous formaldehyde solution (2 mL) was slowly added dropwise at 30-35° C., and then the temperature was increased to 40° C. to continue the reaction. After the reaction was complete by Thin-Layer Chromatography monitoring, the reaction mixture was cooled to room temperature, and slowly poured into ice water (10 mL), and fully stirred. The solid was precipitated, and filtered, and the filter cake was purified by column chromatography on silica gel to obtain 0.52 g of the target compound as a white solid, with 92% yield.

$^1$H NMR (300 MHz, CDCl$_3$, ppm): 8.28 (d, 1H), 8.13 (s, 1H), 7.90 (s, 1H), 7.40-7.36 (m, 1H), 7.19-7.14 (m, 1H), 6.93-6.88 (m, 1H), 4.13 (br. s, 1H), 2.94 (s, 3H).

4) Preparation of N-(2-bromo-4-heptafluoroisopropyl-6-trifluoromethylphenyl)-2-fluoro-3-(N-methyl-2,2-difluoro-1,3-benzodioxole-5-carboxamido) Benzamide (Compound I-45)

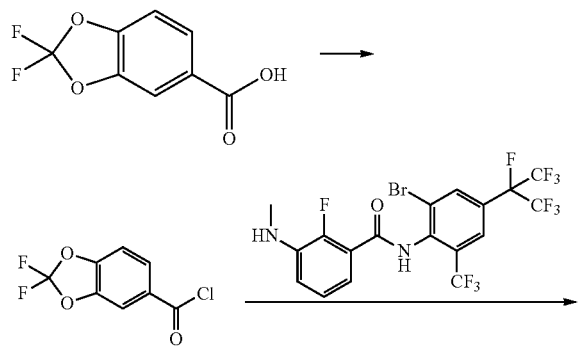

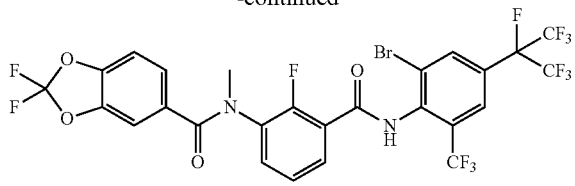

2,2-difluoro-1,3-benzodioxole-5-carboxylic acid (0.21 g, 1.0 mmol), thionyl chloride (1.02 g), toluene (10 mL) and DMF (1 drop) were added to the reaction flask. The reaction mixture were heated to 80° C. to react for 4 hours, and decompressed to distill off thionyl chloride. The acyl chloride obtained was dissolved in toluene (20 mL), and then N-(2-bromo-4-heptafluoroisopropyl-6-trifluoromethylphenyl)-2-fluoro-3-methylaminobenzamide (0.51 g, 0.9 mmol) was added. The resulting mixture was heated to 110° C. to react. After the reaction was complete by Thin-Layer Chromatography monitoring, the reaction mixture was cooled to room temperature, and fully stirred. The solid was gradually precipitated, and filtered. The filter cake was purified by column chromatography on silica gel to obtain 0.57 g of the target compound as a white solid, with 84% yield (calculated based on the N-(2-bromo-4-heptafluoroisopropyl-6-trifluoromethylphenyl)-2-fluoro-3-methylaminobenzamide).

$^1$H NMR (300 MHz, CDCl$_3$, ppm): 8.13-8.04 (m, 3H), 7.91 (s, 1H), 7.52-7.47 (m, 1H), 7.37-7.31 (m, 1H), 7.20 (s, 1H), 7.02 (d, 1H), 6.87 (d, 1H), 3.51 (s, 3H).

Embodiment 2: Preparation of Compound 1-2

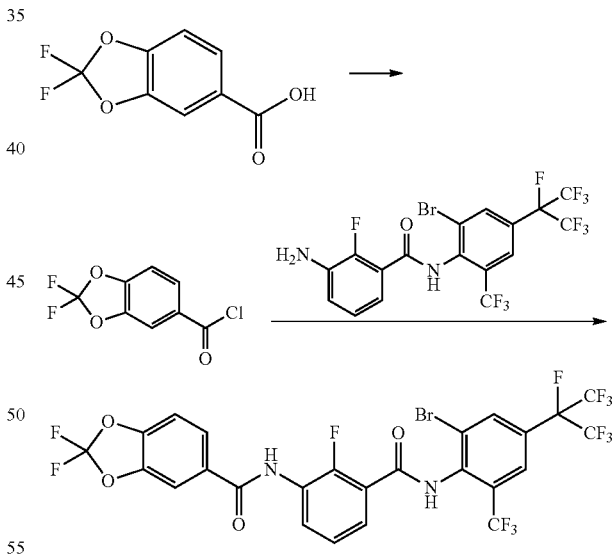

2,2-difluoro-1,3-benzodioxole-5-carboxylic acid (0.21 g, 1.0 mmol), thionyl chloride (1.08 g), toluene (10 and DMF (1 drop) were added to the reaction flask. The reaction mixture was heated to 80° C. to react for 4 hours, and decompressed to distill off thionyl chloride. The obtained acyl chloride was dissolved in toluene (20 mL), and then N-(2-bromo-4-heptafluoroisopropyl-6-trifluoromethylphenyl)-3-amino-2-fluorobenzamide (0.50 g, 0.9 mmol) was added. The resulting mixture was heated to 110° C. to react. After the reaction was complete by Thin-Layer Chromatography monitoring, the reaction mixture was cooled to room temperature, and fully stirred. The solid was gradually precipitated, and filtered. The filter cake was purified by column chromatography on silica gel to obtain 0.55 g of the target compound as a white solid, with 83% yield (calculated based on the N-(2-bromo-4-heptafluoroisopropyl-6-trifluoromethyl phenyl)-3-amino-2-fluorobenzamide).

$^1$H NMR (300 MHz, CDCl$_3$, ppm): 8.20 (s, 1H), 7.99 (s, 1H), 7.47 (d, 1H), 7.38 (s, 1H), 6.96-6.80 (m, 4H), 6.71-6.65 (m, 1H).

Embodiment 3: Preparation of Compound I-51

1) Preparation of N-(2,6-dibromide-4-heptafluoroisopropylphenyl)-2-fluoro-3-nitrobenzamide

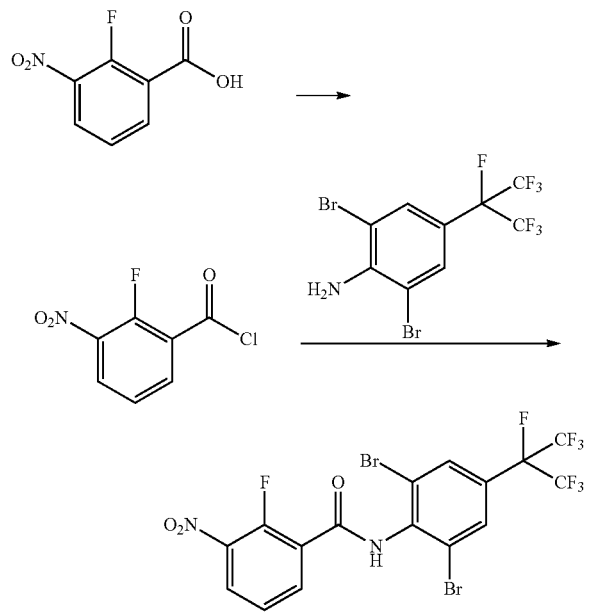

2-fluoro-3-nitrobenzoic acid (3.71 g, 20.0 mmol), thionyl chloride (16.05 g) and DMF (0.20 g) were added to a reaction flask. The reaction mixture was heated to 80° C. to react for 6 hours, and decompressed to distill off thionyl chloride to obtain acid chloride. Acetonitrile (40 mL), 2,6-dibromo-4-heptafluoroisopropyl aniline (4.23 g, 10.0 mmol) and potassium iodide (0.42 g) were added. The resulting mixture was heated to 100° C. to react. After the reaction was complete by Thin-Layer Chromatography monitoring, the mixture was cooled to room temperature, taking about 8 hours. The reaction solution was cooled to room temperature, filtered to remove insolubles, and decompressed to distill off acetonitrile. Ethyl acetate (30 mL) was added to dissolve. The resulting solution was washed successively with a saturated aqueous sodium bicarbonate solution and saturated salt solution to separate an organic phase. The organic phase was dried over anhydrous magnesium sulfate, filtered and decompressed to distill off organic solvents. The residue was purified by column chromatography on silica gel to obtain 5.42 g of the target compound as a white solid, with 91% yield (calculated based on the 2,6-dibromo-4-heptafluoroisopropyl aniline).

$^1$H NMR (300 MHz, CDCl$_3$, ppm): 8.51-8.46 (m, 1H), 8.31-8.27 (m, 1H), 8.16 (d, 1H), 7.91 (s, 2H), 7.55-7.51 (m, 1H).

2) Preparation of N-(2,6-dibromide-4-heptafluoroisopropylphenyl)-3-amino-2-fluorobenzamide

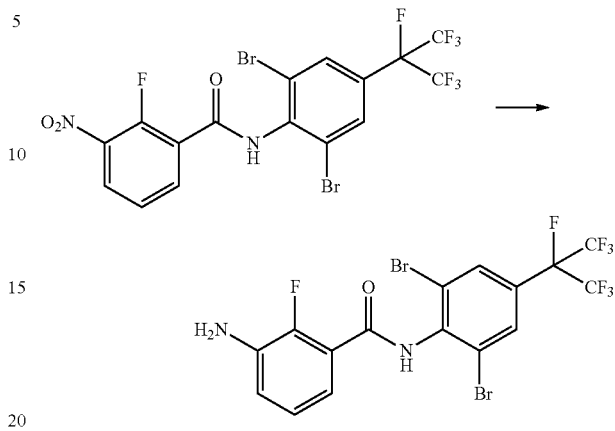

To the reaction flask, N-(2,6-dibromide-4-heptafluoroisopropylphenyl)-2-fluoro-3-nitrobenzamide (1.48 g, 2.5 mmol), dioxane (10 mL) and stannous chloride (2.28 g, 10.0 mmol) were added, and then concentrated hydrochloric acid (2 mL) was slowly added dropwise. The reaction mixture was heated to 60-65° C. to react. After the reaction was complete by Thin-Layer Chromatography monitoring, the mixture was cooled to room temperature, and then poured into ice water (15 mL). Ethyl acetate (30 mL) was added. Sodium hydroxide was slowly added to neutralize to pH=8-9. After the resulting mixture with precipitate was filtered through diatomite, the filter cake was washed with ethyl acetate and the filtrate was layered. The organic phase was dried over anhydrous magnesium sulfate and decompressed to distill off organic solvents. The residue was purified by column chromatography on silica gel to obtain 1.30 g of the target compound as a yellow solid, with 92% yield.

$^1$H NMR (300 MHz, CDCl$_3$, ppm): 8.28 (d, 1H), 8.13 (s, 1H), 7.90 (s, 1H), 7.49-7.47 (m, 1H), 7.13-7.10 (m, 1H), 7.04-6.99 (m, 1H), 3.94 (br. s, 1H).

3) Preparation of N-(2,6-dibromide-4-heptafluoroisopropylphenyl)-2-fluoro-3-(methylamino)benzamide

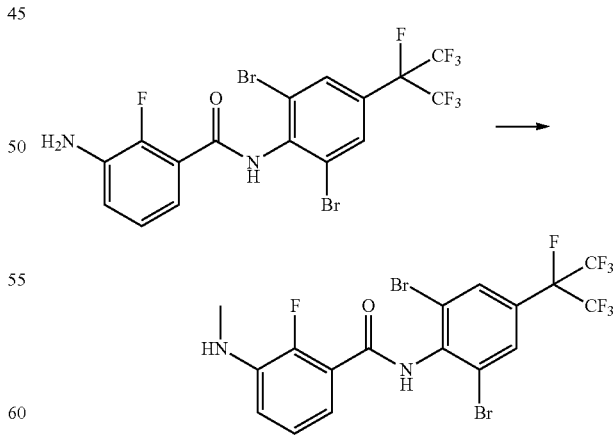

Concentrated sulfuric acid ($^3$ mL) and N-(2,6-dibromide-4-heptafluoroisopropylphenyl)-3-amino-2-fluorobenzamide (0.56 g, 1.0 mmol) were added to the reaction flask, and fully stirred for dissolving. Aqueous formaldehyde solution (2 mL) was slowly added dropwise at 30-35° C., and then the temperature was increased to 40° C. to continue the reaction. After the reaction was complete by Thin-Layer Chromatography monitoring, the reaction mixture was cooled to room temperature, and slowly poured into ice water (10 mL), and fully stirred. The solid was precipitated, and filtered, and the filter cake was purified by column chromatography on silica gel to obtain 0.54 g of the target compound as a white solid, with 93% yield.

$^1$H NMR (300 MHz, CDCl$_3$, ppm): 8.20 (d, 1H), 7.87 (s, 2H), 7.43-7.29 (m, 1H), 7.20-7.18 (m, 1H), 6.93-6.88 (m, 1H), 4.91-4.87 (m, 1H), 2.94 (d, 3H).

4) Preparation of N-(2,6-dibromide-4-heptafluoroisopropylphenyl)-2-fluoro-3-(N-methyl-2,2-difluoro-1,3-benzodioxol e-5-carboxamido)benzamide (Compound I-51)

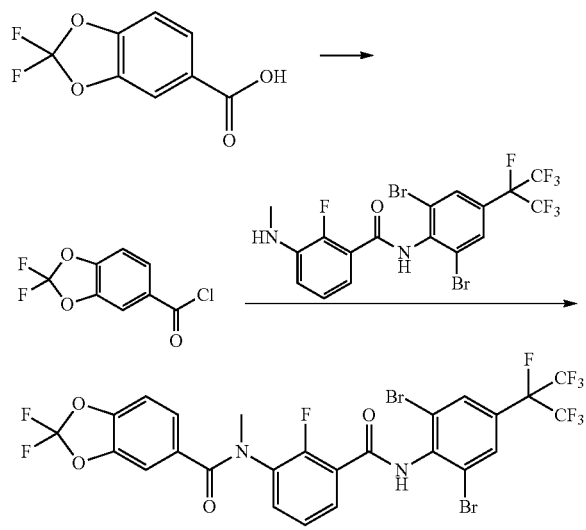

2,2-difluoro-1,3-benzodioxole-5-carboxylic acid (0.21 g, 1.0 mmol), thionyl chloride (1.01 g), toluene (10 mL) and DMF (1 drop) were added to the reaction flask. The reaction mixture were heated to 80° C. to react for 4 hours, and decompressed to distill off thionyl chloride. The acyl chloride obtained was dissolved in toluene (20 mL), and then N-(2,6-dibromide-4-heptafluoroisopropylphenyl)-2-fluoro-3-methylaminobenzamide (0.52 g, 0.9 mmol) was added. The resulting mixture was heated to 110° C. to react. After the reaction was complete by Thin-Layer Chromatography monitoring, the reaction mixture was cooled to room temperature, and fully stirred. The solid was gradually precipitated, and filtered. The filter cake was purified by column chromatography on silica gel to obtain 0.60 g of the target compound as a white solid, with melting point of 157-158 V. and 87% yield (calculated based on the N-(2,6-dibromide-4-heptafluoroisopropylphenyl)-2-fluoro-3-methylaminobenzamide).

$^1$H NMR (300 MHz, CDCl$_3$, ppm): 8.09-8.04 (m, 2H), 7.87 (s, 2H), 7.47-7.43 (m, 1H), 7.34-7.29 (m, 1H), 7.20 (s, 1H), 7.05 (d, 1H), 6.89 (d, 1H), 3.50 (s, 3H), Embodiment 4: Preparation of Compound 1-8

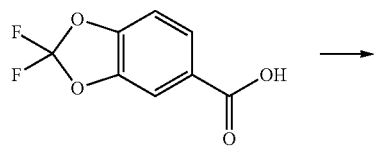

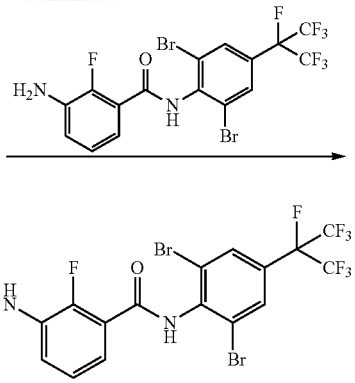

2,2-difluoro-1,3-benzodioxole-5-carboxylic acid (0.21 g, 1.0 mmol), thionyl chloride (1.06 g), toluene (10 mL) and DMF (1 drop) were added to the reaction flask. The reaction mixture was heated to 80° C. to react for 4 hours, and decompressed to distill off thionyl chloride. The obtained acyl chloride was dissolved in toluene (20 mL), and then N-(2,6-dibromide-4-heptafluoroisopropylphenyl)-3-amino-2-fluorobenzamide (0.51 g, 0.9 mmol) was added. The resulting mixture was heated to 110° C. to react. After the reaction was complete by Thin-Layer Chromatography monitoring, the reaction mixture was cooled to room temperature, and fully stirred. The solid was gradually precipitated, and filtered, The filter cake was purified by column chromatography on silica gel to obtain 0.54 g of the target compound as a white solid, with melting point of 176-177° C. and 80% yield (calculated based on the N-(2,6-dibromide-4-heptafluoroisopropylphenyl)-3-amino-2-fluorobenzamide). $^1$H NMR (300 MHz, CDCl$_3$, ppm): 8.57-8.52 (m, 1H), 8.17-8.12 (m, 2H), 7.90-7.86 (m, 3H), 7.70-7.68 (m, 2H), 7.39-7.34 (m, 1H), 7.20 (d, 1H).

Embodiment 5: Preparation of Compound 1-5

1) Preparation of Methyl-3-(2,2-difluoro-1,3-benzodioxole-5-carboxamido)-2-fluorobenzoate (compound II-1)

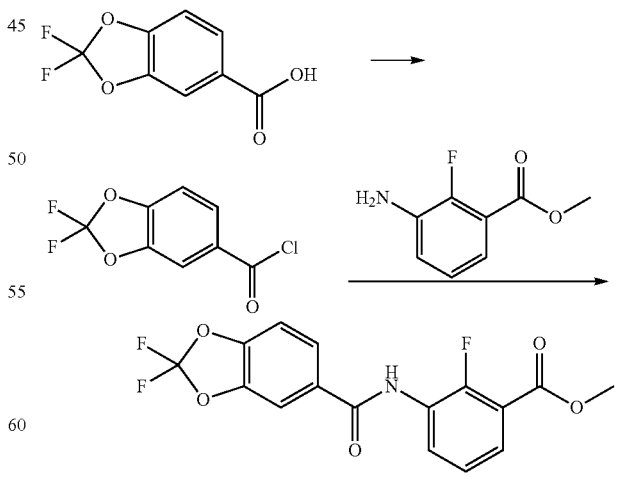

2,2-difluoro-1,3-benzodioxole-5-carboxylic acid (4.08 g, 20 mmol), thionyl chloride (21.40 g) and DMF (0.10 g) were added to the reaction flask. The reaction mixture was refluxed for 6 hours, and decompressed to distill off thionyl chloride to obtain acyl chloride. Toluene (30 mL) and methyl-3-amino-2-fluorobenzoate (3.42 g, 20 mmol) were added. The resulting mixture was refluxed for 3 hours, and cooled to room temperature. The solid was precipitated and filtered. The filter cake was purified by column chromatography on silica gel to obtain 5.89 g of the target compound as a white solid, with melting point of 130-131° C. and 82% yield (calculated based on the methyl-3-amino-2-fluorobenzoate).

$^1$H NMR (300 MHz, CDCl$_3$, ppm): 10.15 (s, 1H), 7.93-7.87 (m, 3H), 7.74-7.69 (m, 1H), 7.41 (d, 1H), 7.34-7.28 (m, 1H), 3.89 (s, 3H).

2) Preparation of 3-(2,2-difluoro-1,3-benzodioxole-5-carboxamido)-2-fluorobenzoic Acid (Compound II-7)

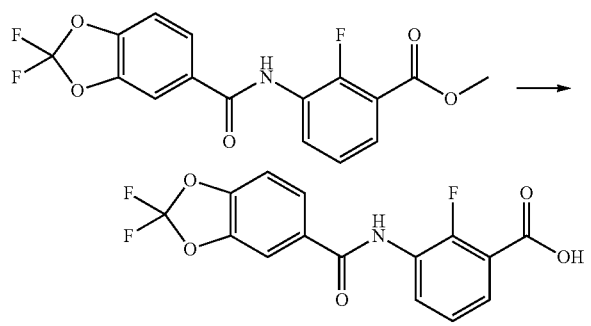

Sodium hydroxide (0.62 g, 15 mmol), water (10 mL) and methanol (10 mL) were added to the reaction flask. After the sodium hydroxide was dissolved, methyl-3-(2,2-difluoro-1,3-benzodioxole-5-carboxamido)-2-fluorobenzoate (3.57 g, 10 mmol) was added. The reaction mixture was heated to 60-65° C. to react. After the reaction was complete by Thin-Layer Chromatography monitoring, the reaction mixture was cooled to room temperature. Ethyl acetate (5 mL) was added. The resulting reaction solution was extracted and layered. The aqueous phase was stirred and also adjusted to pH=2-3 with 1N hydrochloric acid. The solid was precipitated, and filtered. The filter cake was dried to obtain 3.13 g of the target compound as a white solid, with melting point of 266-267° C. and 91% yield.

$^1$H NMR (300 MHz, CDCl$_3$, ppm): 13.18 (br. s, 1H), 10.21 (s, 1H), 7.95-7.90 (m, 2H), 7.84-7.80 (m, 1H), 7.74-7.69 (m, 1H), 7.51 (d, 1H), 7.31-7.26 (m, 1H).

3) Preparation of N-(2-bromo-6-iodo-4-perfluoroisopropylphenyl)-3-(2,2-difluoro-1,3-benzodioxole-5-carboxamido)-2-fluorobenzamide (Compound 1-5)

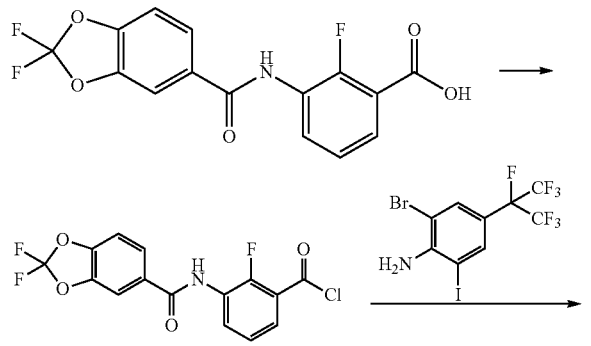

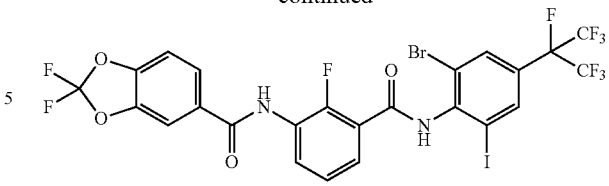

3-(2,2-difluoro-1,3-benzodioxole-5-carboxamido)-2-fluorobenzoic acid (2.06 g, 6.0 mmol), thionyl chloride (3.60 g), toluene (10 mL) and DMF (1 drop) were added to the reaction flask. The reaction mixture was heated to 100° C. to react for 4 hours, and decompressed to distill off thionyl chloride and toluene to obtain acyl chloride (compound II-9) as a white solid (melting point of 155-156° C.). Acetonitrile (15 mL), 2-bromo-6-iodo-4-perfluoroisopropyl aniline (1.88 g, 4.0 mmol) and potassium iodide (0.17 g, 1.0 mmol) were added. The resulting mixture was refluxed to react for 8 hours and cooled to room temperature. Ethyl acetate (30 mL) was added. The resulting solution was washed successively with a saturated aqueous sodium bicarbonate solution and saturated salt solution. The organic phase was dried over anhydrous magnesium sulfate, filtered and decompressed to distill off solvents. The residue was purified by column chromatography on silica gel to obtain 2.58 g of the target compound as a white solid, with 81% yield (calculated based on the 2-bronco-6-iodo-4-perfluoroisopropyl aniline).

Compound II-9: $^1$H NMR (300 MHz, CDCl$_3$, ppm): 8.80-8.75 (m, 1H), 8.05 (br. s, 1H), 7.90-7.85 (m, 1H), 7.66-7.64 (m, 2H), 7.39-7.33 (m, 1H), 7.20 (d, 1H), Compound I-5: $^1$H NMR (300 MHz, CDCl$_3$, ppm): 8.62-8.57 (m, 8.12-8.05 (m, 3H), 7.96-7.91 (m, 2H), 7.70-7.68 (m, 2H), 7.42-7.36 (m, 1H), 7.21 (d, 1H).

Embodiment 6: Preparation of Compound 1-48

1) Preparation of Methyl-2-fluoro-3-(N-methyl-2,2-difluoro-1,3-benzodioxole-5-carboxamido) benzoate (compound II-12)

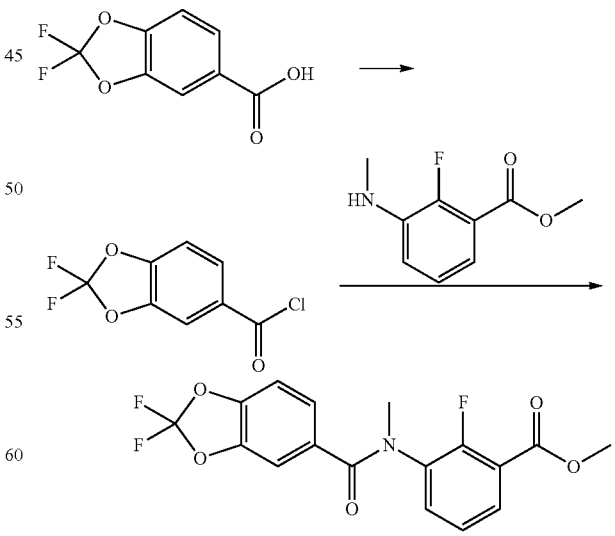

2,2-difluoro-1,3-benzodioxole-5-carboxylic acid (4.08 g, 20 mmol), thionyl chloride (21.40 g) and DMF (0.10 g) were added to the reaction flask. The reaction mixture was refluxed for 6 hours, and decompressed to distill off thionyl chloride to obtain acyl chloride. Toluene (30 mL) and methyl-2-fluoro-3-methylaminobenzoate (3.70 g, 2.0 mmol) were added. The resulting mixture was refluxed for 3 hours, and cooled to room temperature. The solid was precipitated and filtered. The filter cake was purified by column chromatography on silica gel to obtain 5.90 g of the target compound as a white solid, with 79% yield (calculated based on the methyl-2-fluoro-3-methylaminobenzoate).

$^1$H NMR (300 MHz, CDCl$_3$, ppm): 7.86-7.80 (m, 1H), 7.26-7.22 (m, 1H), 7.14-7.09 (m, 2H), 7.03 (d, 1H), 6.85 (d, 1H), 3.94 (s, 3H), 3.42 (s, 3H).

2) Preparation of 2-fluoro-3-(N-methyl-2,2-difluoro-1,3-benzodioxole-5-carboxamido)benzoic Acid (Compound II-18)

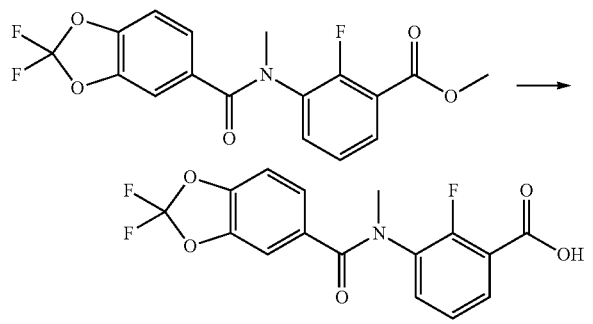

Sodium hydroxide (0.62 g, 15 mmol), water (10 mL) and methanol (10 mL) were added to the reaction flask. After the sodium hydroxide was dissolved, methyl-2-fluoro-3-(N-methyl-2,2-difluoro-1,3-benzodioxole-5-carboxamido) benzoate (3.71 g, 10 mmol) was added. The reaction mixture was heated to 60-65° C. to react. After the reaction was complete by Thin-Layer Chromatography monitoring, the reaction mixture was cooled to room temperature. Ethyl acetate (5 mL) was added. The resulting reaction solution was extracted and layered. The aqueous phase was stirred and also adjusted to pH=2-3 with 1N hydrochloric acid. The solid was precipitated, and filtered. The filter cake was dried to obtain 3.15 g of the target compound as a white solid, with 88% yield.

1H NMR (300 MHz, CDCl$_3$, ppm): 13.09 (br. s, 1H), 7.86-7.83 (m, 1H), 7.76-7.71 (m, 2H), 7.59-7.55 (m, 1H), 7.39 (d, 1H), 7.21-7.16 (m, 1H), 3.32 (s, 3H).

3) Preparation of N-(2-bromo-6-iodo-4-perfluoroisopropylphenyl)-2-fluoro-3-(N-methyl-2,2-difluoro-1,3-benzodioxole-5-carboxamido)benzamide (compound I-48)

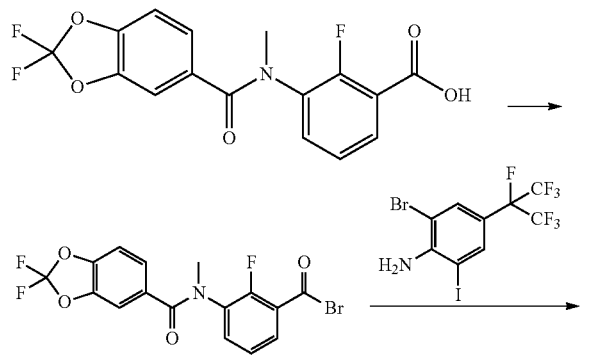

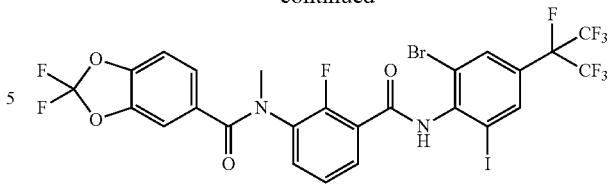

2-fluoro-3-(N-methyl-2,2-difluoro-1,3-benzodioxole-5-carboxamido)benzoic acid (2.14 g, 6.0 mmol), phosphorus tribromide (0.42 g) and toluene (10 mL) were added to the reaction flask. The reaction mixture was heated to 100° C. to react for 4 hours, and decompressed to distill off toluene to obtain acyl bromide (compound II-21) as a yellow oil. Acetonitrile (15 mL), 2-bromo-6-iodo-4-perfluoroisopropylaniline (1.88 g, 4.0 mmol) and potassium iodide (0.17 g, 1.0 mmol) were added. The resulting mixture was refluxed to react for 8 hours, and cooled to room temperature. Ethyl acetate (30 mL) was added. The reaction solution was washed successively with a saturated aqueous sodium bicarbonate solution and saturated salt solution. The organic phase was dried over anhydrous magnesium sulfate, filtered and decompressed to distill off solvents. The residue was purified by column chromatography on silica gel to obtain 2.64 g of the target compound as a white solid, with melting point of 185-186° C. and 81% yield (calculated based on the 2-bromo-6-iodo-4-perfluoroisopropylaniline).

Compound 1-48: $^1$H NMR (300 MHz, CDCl$_3$, ppm): 8.10-8.03 (m, 3H), 7.89 (s, 1H), 7.49-7.44 (m, 1H), 7.35-7.30 (m, 1H), 7.20 (s, 1H), 7.05 (d, 1H), 6.88 (d, 1H), 3.50 (s, 3H).

Embodiment 7: Preparation of Compound 1-8

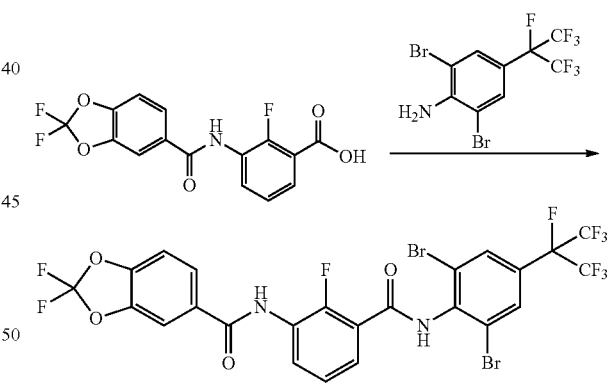

3-(2,2-difluoro-1,3-benzodioxole-5-carboxamido)-2-fluorobenzoic Acid (2.06 g, 6.0 mmol), p-nitrobenzenesulfonyl chloride (1.33 g, 6.0 mmol), acetonitrile (25 mL) and triethylamine (0.67 g, 6.6 mmol) were added to the reaction flask. The reaction mixture was refluxed to react for 4 hours. 2,6-dibromide-4-heptafluoroisopropylaniline (1.69 g, 4.0 mmol) and potassium iodide (0.17 g, 1.0 mmol) were added, and the resulting mixture was continuously refluxed to react for 24 hours, and cooled to room temperature. Ethyl acetate (30 mL) was added. The reaction solution was washed successively with a saturated aqueous sodium bicarbonate solution and saturated salt solution. The organic phase was dried over anhydrous magnesium sulfate, filtered and decompressed to distill off solvents. The residue was purified by column chromatography on silica gel to obtain 1.82 g of the target compound as a white solid, with melting point of 176-177° C. and 60% yield (calculated based on the 2,6-dibromide-4-heptafluoroisopropylaniline).

Embodiment 8: Preparation of Compound I-44

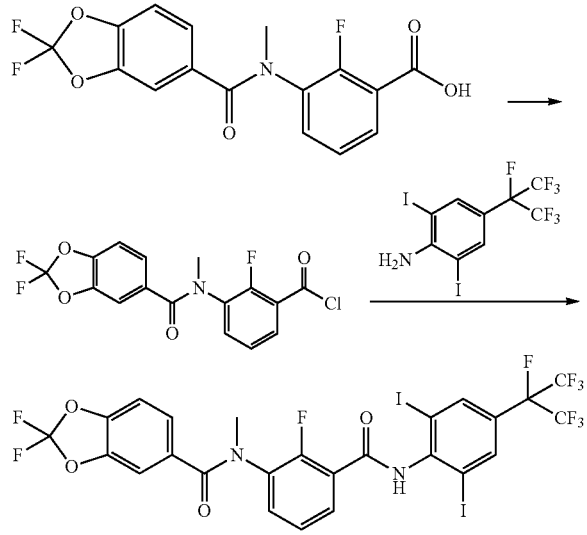

2-fluoro-3-(N-methyl-2,2-difluoro-1,3-benzodioxole-5-carboxamido)benzoic acid (2.14 g, 6.0 mmol), thionyl chloride (3.60 g) and toluene (10 mL) were added to the reaction flask. The reaction mixture was heated to 100° C. to react for 6 hours, and decompressed to distill off thionyl chloride and toluene to obtain acyl chloride (compound II-20) as a yellow oil. Acetonitrile (15 mL), 2,6-diiodo-4-heptafluoroisopropylaniline (2.07 g, 4.0 mmol) and potassium iodide (0.17 g, 1.0 mmol) were added. The resulting mixture was refluxed to react for 8 hours, and cooled to room temperature. Ethyl acetate (30 mL) was added. The reaction solution was washed successively with a saturated aqueous sodium bicarbonate solution and saturated salt solution. The organic phase was dried over anhydrous magnesium sulfate, filtered and decompressed to distill off solvents. The residue was purified by column chromatography on silica gel to obtain 2.70 g of the target compound as a white solid, with 78% yield (calculated based on the 2,6-diiodo-4-heptafluoroisopropylaniline).

Compound I-44: $^1$H NMR (300 MHz, CDCl$_3$, ppm): 8.08-8.03 (m, 2H), 7.86 (s, 2H), 7.45-7.41 (m, 1H), 7.33-7.28 (m, 1H), 7.20 (s, 1H), 7.05 (d, 1H), 6.90 (d, 1H), 3.50 (s, 3H).

At the same time, other compounds shown in the general formula I can also be prepared in the methods described above.

Determination of Biological Activity

Embodiment 9 Determination of Insecticidal Activity

According to the solubility of test compounds, the compounds are dissolved in acetone or dimethyl sulfoxide, and then diluted with 0.1% aqueous solution of Tween 80 to form a required concentration of 50 ml test liquid, The content of the acetone or the dimethyl sulfoxide in the total solution is not more than 10%.

Embodiment 9.1 Determination of Activity Against Armyworm

The middle leaves of fresh corns were cut into small sections of 3 cm, and dipped into a solution of the required concentration of test compounds for 10 seconds. After dried in shade, the middle leaves were placed in a 9 cm diameter petri dish provided with filter paper. Fourteen regular healthy test insects (third instar) were put into the leaves. Four replicates were set for each treatment. The pure water treatment was set as control check. The treated discs were placed in a chamber of is 24° C., 60%-70% relative humidity and day light. After 72 hours, the number of surviving insects was investigated, and the mortality rate was calculated.

Among some of the testing compounds, compounds I-2, I-5, I-8, I-44, I-45, I-48 and I-51 showed over 90% mortality rates against armyworm at 0.3 mg/L.

According to the above test method, compounds I-8 and I-51 and known compounds KC$_1$ (compound 160 in US2014206727A1) and KC$_3$ (compound 3-14 in U.S. Pat. No. 8,853,440B2) were selected for parallel determination of activity against armyworm. See Table 1 for test results.

TABLE 1

Parallel Determination Results of Activity of Compounds I-8, I-51, KC$_1$ and KC$_3$ against Armyworm (Mortality rate, %)

| Compound | Mortality rate (%) | |
|---|---|---|
| | 0.3 mg/L | 0.1 mg/L |
| Compound I-8 | 100 | 100 |
| Compound I-51 | 100 | 85.7 |
| KC$_1$ | 0 | 0 |
| KC$_3$ | 64.3 | 28.6 |

Embodiment 9.2 Determination of Activity Against Diamondback Moth

The leaves of cabbage grown in greenhouse were selected, removed the surface waxy layers, punched into circular leaf discs with a diameter of 2 cm by using a puncher, and dipped into a solution of the required concentration of test compounds for 10 seconds. After dried in shade, the circular leaf discs were placed in a 9 cm diameter petri dish provided with filter paper. Ten regular healthy test insects (second instar) were put into the leaf discs. Four replicates were set for each treatment. The pure water treatment was set as control check. The treated discs were placed in a chamber of 24° C., 60%-70% relative humidity and day light. After 72 hours, the number of surviving insects was investigated, and the mortality rate was calculated.

Among some of the testing compounds, compounds I-2, I-5, I-8, I-44, I-45, I-48 and I-51 showed over 90% mortality rates against diamondback moth at 1 mg/L.

Embodiment 9.3 Determination of Activity Against Beet Armyworm

The cabbage leaves were punched into circular leaf discs with a diameter of 1 cm by using a puncher. A certain concentration of test compound was sprayed on both sides of each leaf disc at a spray volume of 0.5 ml by a handheld Airbrush. After the leaf discs were dried in shade, 12 test insects (third instar) were put into the leaf discs. Three replicates were set for each treatment. The pure water treatment was set as control check. The treated discs were placed in a chamber of 24° C., 60%-70% relative humidity and day light. After 96 hours, the number of surviving insects was investigated, and the mortality rate was calculated. See Table 2 for parallel determination results of activity of compounds 1-8 and $KC_2$ (compound 3-1 in U.S. Pat. No. 8,853,440B2) against beet armyworm.

TABLE 2

Parallel Determination Results of Activity of Compounds I-8 and $KC_2$ against Beet Armyworm (Mortality rate, %)

| Compound | Mortality rate (%) | |
| --- | --- | --- |
| | 1 mg/L | 0.2 mg/L |
| Compound I-8 | 91.7 | 83.3 |
| $KC_2$ | 83.3 | 66.7 |

Embodiment 9.4 Determination of Activity Against Green Peach Aphid

A layer of filter paper was covered on the bottom of the 6 cm diameter petri dish. To the petri dish, a proper amount of tap water was added dropwise for moisture retention. Cabbage leaves, on which 15-30 aphids exist, with a suitable size (about 3 cm in diameter) were cut from the cabbage plants breeding peach aphids. After winged aphids and the aphids on the front surface of the leaves were removed, the leaves were placed in the petri dish in a manner of backing on to the petri dish, and sprayed with a handheld Airbrush, with a pressure of 10 psi (about 0.7 kg/cm$^2$) and a spray volume of 0.5 ml, Three replicates were set for each treatment. After treatment, the cabbage leaves were placed in a standard observation room. After 48 hours, the number of surviving aphids was investigated, and the mortality rate was calculated.

Among some of the testing compounds, compounds I-8 and I-51 showed over 80% mortality rates against green peach aphid at 10 mg/L.

Embodiment 9.5 Determination of Activity Against Rice Leaf Folder in Field Trial A certain concentration of test compounds was sprayed on the leaf surfaces in the peak of the hatching period of the rice leaf folders, with a spray volume of 450 L per hectare. The area of a rice plot was 32 square meters. Three replicates were set for each treatment. After 15 days, the number of surviving rice leaf folders was investigated, and the mortality rate was calculated. See Table 3 for parallel determination results of activity of compounds I-8 and $KC_2$ against rice leaf folder.

TABLE 3

Parallel Determination Results of Activity of Compounds I-8 and $KC_2$ against Rice Leaf Folder in Field Trial (Mortality rate, %)

| Compound | Mortality rate (%) | |
| --- | --- | --- |
| | 45 g/ha | 30 g/ha |
| Compound I-8 | 85 | 83 |
| $KC_2$ | 82 | 79 |

Embodiment 10 Determination of Acaricidal Activity

According to the solubility of test compounds, the compounds are dissolved in acetone or dimethyl sulfoxide, and then diluted with 0.1% aqueous solution of Tween 80 to form a required concentration of 50 ml test liquid. The content of the acetone or the dimethyl sulfoxide in the total solution is not more than 10%.

The adult spider mites were put into two true leaves of bean plants. After the number of mites was investigated, the solution of certain concentrations of test compounds was sprayed by using a handheld Airbrush. Three replicates were set for each treatment. Then the leaves were maintained in a standard observation room. After 72 hours, the number of surviving mites was observed, and the mortality rate was calculated.

The control compounds $C_1$ and $C_2$ (structural formulas are as follows) were non-list compounds included in the scope disclosed by the patent AU2004315003B2. See Table 4 for parallel determination results of activity of compounds I-8, $KC_1$, $KC_2$, $KC_3$, $C_1$ and $C_2$ against adult spider mite.

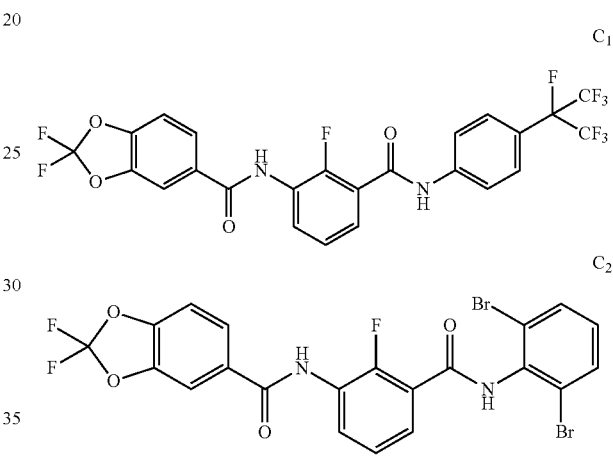

TABLE 4

Parallel Determination Results of Activity of Compounds I-8, $KC_1$, $KC_2$, $KC_3$, $C_1$ and $C_2$ against Adult Spider Mite (Mortality rate, %)

| Compound | Mortality rate (%) | | |
| --- | --- | --- | --- |
| | 600 mg/L | 100 mg/L | 10 mg/L |
| Compound I-8 | 100 | 100 | 93.3 |
| $KC_1$ | 0 | 0 | 0 |
| $KC_2$ | 0 | 0 | 0 |
| $KC_3$ | 0 | 0 | 0 |
| $C_1$ | 0 | 0 | 0 |
| $C_2$ | 0 | 0 | 0 |

Embodiment 11 Determination of Activity Against Houseflylarva

Third instar housefly larvae were tested by a feed poisoning method. 1000 mg/L, of acetone solution of the test compounds was diluted into a required concentration of test liquid by using a certain concentration of milk powder emulsion according to a test design dose. The test liquid was uniformly added to a 6 cm diameter petri dish provided with filter paper by using a pipette, with 1 ml per dish. The third instar housefly larvae were put into the petri dish. Three replicates were set for each treatment. Then the petri dishes were maintained in a standard observation room. After 72 hours, the number of surviving housefly larvae was investigated, and the mortality rate was calculated. See Table 5 for parallel determination results of activity of compounds I-51 and KC$_2$ against housefly larva.

TABLE 5

Parallel Determination Results of Activity of Compounds I-51 and KC$_2$ against Housefly Larva (Mortality rate, %)

| Compound | Mortality rate (%) | | |
|---|---|---|---|
| | 10 mg/L | 3 mg/L | 1 mg/L |
| Compound I-51 | 100 | 90.5 | 75 |
| KC$_2$ | 100 | 69.6 | 50 |

Embodiment 12 Determination of Fungicidal Activity

According to the solubility of test compounds, the compounds are dissolved in acetone, methanol or N,N-Dimethylformamide, and then diluted with 0.1% aqueous solution of Tween 80 to form a required concentration of 50 ml test liquid. The content of the acetone, methanol or N,N-Dimethylformamide in the total solution is not more than 5%.

Cucumber seedlings that grew consistently at two-leaf state were selected, and sprayed with a certain concentration of test compounds. After 24 hours from treatment, the cucumber seedlings were inoculated with cucumber downy mildew spore suspension, and then put into an artificial climate chamber for culture. After infested by diseases, the cucumber seedlings were transferred into a greenhouse for normal culture. After 5 days, the control effect was investigated by a visual method according to the incidence of the control check. The control effect was recorded with 100%-0.100% represented no infection, and 0 represented the infection degree of treatment was equivalent to that of the control check.

Among some of the testing compounds, compounds I-8 and I-51 showed over 90% control effects against cucumber downy mildew at 400 mg/L.

The other compounds shown in the general formula I and obtained by the synthetic method described in the present invention also have the above corresponding characteristics, and achieve unexpected effects.

We claim:
1. A method for controlling fungus on plants comprising, applying a composition comprising an effective amount of a piperonylic acid derivative of general formula I:

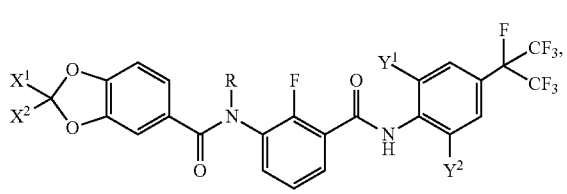

where $X^1$ and $X^2$ are F; R is H or methyl; and $Y^1$ and $Y^2$ are Br, and an acceptable carrier, where the effective amount includes a weight percentage of the piperonylic acid derivative being 1-99% and where the application to the plant is at a dosage of 10 g to 1000 g per hectare.

* * * * *